(12) United States Patent
Wurster et al.

(10) Patent No.: US 7,439,371 B2
(45) Date of Patent: Oct. 21, 2008

(54) INDOL KINASE INHIBITORS

(75) Inventors: Julie A. Wurster, Irvine, CA (US); Richard C. Yee, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 125 days.

(21) Appl. No.: 11/456,630

(22) Filed: Jul. 11, 2006

(65) Prior Publication Data

US 2007/0015748 A1 Jan. 18, 2007

Related U.S. Application Data

(60) Provisional application No. 60/699,065, filed on Jul. 13, 2005.

(51) Int. Cl.
*C07D 403/10* (2006.01)
*C07D 209/34* (2006.01)

(52) U.S. Cl. ............... 548/486; 544/373; 544/295; 544/60; 544/364; 548/364.7; 548/465; 548/408; 548/484; 548/311.1; 548/454; 546/278.4; 549/59; 549/505

(58) Field of Classification Search ........... 548/486, 548/364.7; 544/373
See application file for complete search history.

(56) References Cited

U.S. PATENT DOCUMENTS

| 5,792,783 A | 8/1998 | Tang et al. |
|---|---|---|
| 5,834,504 A | 11/1998 | Tang et al. |
| 5,883,113 A | 3/1999 | Tang et al. |
| 5,883,116 A | 3/1999 | Tang et al. |
| 5,886,020 A | 3/1999 | Tang et al. |
| 6,541,504 B1 | 4/2003 | Andrews et al. |
| 6,559,173 B1 | 5/2003 | Andrews et al. |
| 6,699,863 B1 | 3/2004 | Andrews et al. |
| 6,747,025 B1 | 6/2004 | Andrews et al. |
| 6,765,012 B2 | 7/2004 | Andrews et al. |
| 7,005,444 B2 | 2/2006 | Andrews et al. |
| 7,015,220 B2 | 3/2006 | Andrews et al. |
| 7,060,844 B2 | 6/2006 | Andrews et al. |

FOREIGN PATENT DOCUMENTS

| WO | WO99/15500 | 4/1999 | |
|---|---|---|---|
| WO | WO03/027102 | 4/2003 | |
| WO | WO2006/052936 | * 5/2006 | ........... 514/415 |

OTHER PUBLICATIONS

Plowman et al, "Receptor Tyrosine Kinases as Targets for Drug Intervention", 1994, DN&P 7(6): 334-339.
Bolen, "Nonreceptor tyrosine protein kinases", 1993, Oncogen 8: pp. 2025-2031.

* cited by examiner

*Primary Examiner*—Rebecca L Anderson
*Assistant Examiner*—Yong Chu
(74) *Attorney, Agent, or Firm*—Joel B. German; Dean G. Stathakis; Martin A. Voet

(57) ABSTRACT

The present invention relates to organic molecules capable of modulating tyrosine kinase signal transduction in order to regulate, modulate and/or inhibit abnormal cell proliferation.

7 Claims, No Drawings

INDOL KINASE INHIBITORS

CROSS REFERENCE TO RELATED APPLICATIONS

This application is based on, and claims the benefit of, U.S. Provisional Application No. 60/699,065, filed Jul. 13, 2005, and which is incorporated herein by reference.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phophorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025-2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands soluble receptors and antibodies RNA ligands and tyrosine kinase inhibitors.

More recently, attempts have been made to identify small molecules which act as tyrosine kinase inhibitors. For example, bis monocyclic, bicyclic or heterocyclic aryl compounds, vinylene-azaindole derivatives and 1-cyclopropyl-4-pyridyl-quinolones have been described generally as tyrosine kinase inhibitors. Styryl compounds, styryl-substituted pyridyl compounds certain quinazoline derivatives seleoindoles and selenides, tricyclic polyhydroxylic compounds and benzylphosphonic acid compounds have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Finally, certain small compounds are disclosed in U.S. Pat. Nos. 5,792,783; 5,834,504; 5,883,113; 5,883,116 and 5,886,020 as useful for the treatment of diseases related to unregulated TKS transduction. See also, U.S. Pat. Nos. 6,541,504; 6,559,173; 6,765,012; 6,747,025 and 6,699,863. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration and retinopathy of prematurity, autoimmune diseases and transplant rejection.

Compounds of the general formulas I and II below are useful as kinase inhibitors. As such compounds of formula I and formula II will be useful for treating diseases related to unregulated tyrosine kinase signal transduction, for example, cancer, blood vessel proliferative disorders, fibrotic disorders, and neurodegenerative diseases. In particular compounds of the present invention are useful for the treatment of mesangial cell proliferative disorders and metabolic diseases, diabetic retinopathy, age-related macular degeneration, retinopathy of prematurity, arthritis, restenosis, hepatic cirrhosis, atherosclerosis, psoriasis, diabetes mellitus, wound healing, inflammation and neurodegenerative diseases.

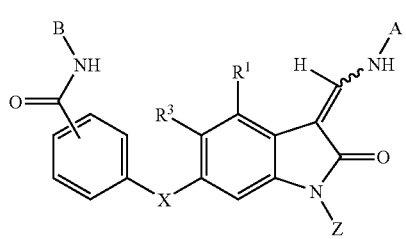

I

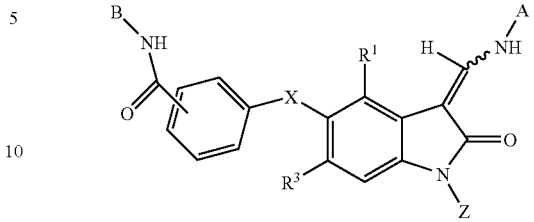

II wherein X is selected from the group consisting of C=O, C=S, $CR^4R^5$, O, S, NH, and $NR^4$;

Z is selected from the group consisting of hydrogen, $C_1$ to $C_8$ alkyl, phenyl, hydroxymethyl, —$CH_2$—N(—$CH_2CH_2W$ $CH_2CH_2$—), $COCH_3$, $CH_2CH_2OH$, and $CH_2CH_2CH_2OH$;

W is selected from the group consisting of O, S, $CH_2$ and $NCH_3$;

$R^1$ is selected from the group consisting of hydrogen and $CH_3$;

$R^3$ is selected from the group consisting of hydrogen, $C_1$ to $C_8$ alkyl, phenyl, hydroxymethyl, $COCH_3$, $CH_2CH_2OH$, $CH_2CH_2CH_2OH$ and $[C(R^2)_2]_cN(R^2)_2$, wherein $R^2$ is selected from the group consisting of hydrogen, halogen, $NO_2$, CN, $C_1$ to $C_4$ alkyl or aryl, and $N(R^2)_2$ may form a 3 to 7 membered heterocyclic ring, for example, pyrrolidine, 3-fluoropyrrolidine, piperidine, 4-fluoropiperidine, N-methylpiperazine, morpholine, 2,6-dimethylmorpholine, thiomorpholine; and said heterocyclic ring may be substituted with one or more of $R^2$; and $[C(R^2)_2]_c$ may form a 3 to 7 membered carbocyclic or heterocyclic ring;

$R^4$ and $R^5$ may be selected from the group consisting of hydrogen, halogen, $NO_2$, CN, $C_1$ to $C_8$ alkyl and aryl; wherein $CR^4R^5$ may form a 3 to 7 membered carbocyclic or heterocyclic ring;

A is

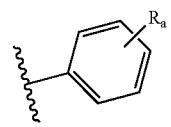

wherein,

R is selected from the group consisting of hydrogen, halogen, $C_1$ to $C_8$ alkyl, $CF_3$, $OCF_3$, $OCF_2H$, $CH_2CN$, CN, $SR^2$, $(CR^7R^8)_cC(O)OR^2$, $C(O)N(R^2)_2$, $(CR^7R^8)_cOR^2$, HNC(O)$R^2$, HN—$C(O)OR^2$, $(CR^7R^8)_cOC(O)(CR^7R^8)_cN(R^2)_2$, $(CR^7R^8)_cN(R^2)_2$, $SO_2(CR^7R^8)_cN(R^2)_2$, $OP(O)(OR^2)_2$, $OC(O)OR^2$, $OCH_2O$, HN—CH=CH, —$N(COR^2)CH_2CH_2$, HC=N—NH, N=CH—S, $O(CR^7R^8)_d$—$R^6$, $(CR^7R^8)_c$—$R^6$ and $(CR^7R^8)_cNR_2(CR^7R^8)_dR^6$ wherein $R^6$ is selected from the group consisting of halogen, 3-fluoropyrrolidinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5(4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N—BOC-pyrrolidinyl, 4-amino-1,2,2,6,6-pentamethylpiperidinyl, 4-aminomethyltetrahydropyran, ethanolamine and alkyl-substituted derivatives thereof, provided said alkyl or phenyl radicals may be substituted with one or two halo, hydroxy or lower alkyl amino radicals or said alkyl radicals may include enchained nitrogen or oxygen atoms, i.e. oxa or imino radicals, as, for example, in polyethylene(oxy)radicals and wherein $R^7$ and $R^8$ may be selected from the group consisting of H, hydroxyl, halogen, e.g. F, and $C_1$ to $C_4$ alkyl and $CR^7R^8$ may form a carbocyclic ring of from 3 to 6 carbons;

B may be selected from the group consisting of hydrogen, hydroxy, $C_1$ to $C_8$ alkyl, aryl and $CR^4R^5$ wherein $CR^4R^5$ may form a 3 to 7 membered carbocyclic or heterocyclic ring, e.g B may be a 5 or 6 membered aryl represented by formula III below:

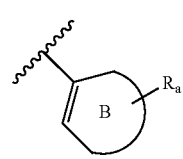

III wherein said aryl is selected from the group consisting of:

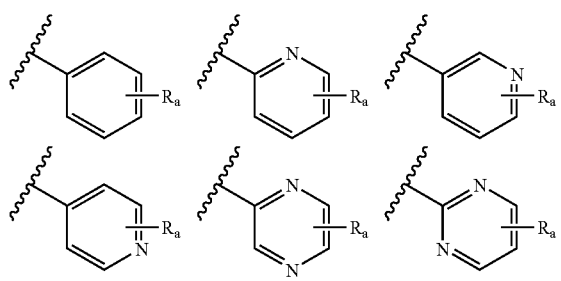

-continued a is 0 or an integer of from 1 to 5, preferably 1 to 3;

c is 0 or an integer of from 1 to 4, d is an integer of from 2 to 5;

the wavy line represents a E or Z bond and pharmaceutically acceptable salts thereof.

Preferably X is S.

DETAILED DESCRIPTION OF THE INVENTION

Specific examples of the above compounds are illustrated but not limited to the illustrative list set forth below:

Substitution Pattern Table

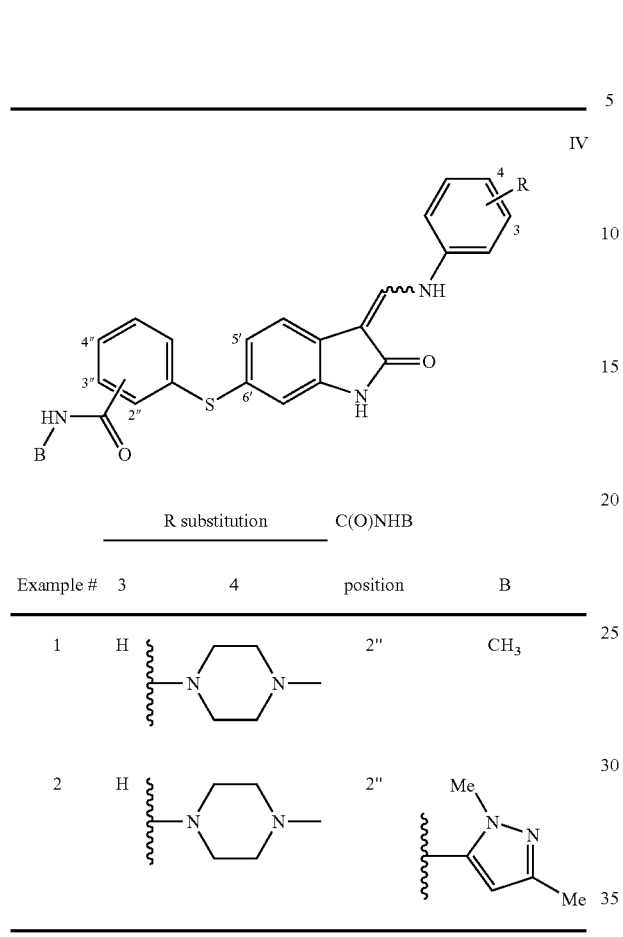

| | R substitution | | C(O)NHB | |
|---|---|---|---|---|
| Example # | 3 | 4 | position | B |
| 1 | H | [4-(4-methyl-piperazin-1-yl)] | 2" | CH₃ |
| 2 | H | [4-(4-methyl-piperazin-1-yl)] | 2" | 1,5-dimethyl-pyrazol-3-yl |

The above compounds may be named as shown below:

Named Compounds:

| Example # | compound name |
|---|---|
| 1 | "N-Methyl-2-(3-{[4-(4-methyl-piperazin-1-yl)-phenylamino]-methylene}-2-oxo-2,3-dihydro-1H-indol-6-ylsulfanyl)-benzamide" |
| 2 | "N-(2,5-Dimethyl-2H-pyrazol-3-yl)-2-(3-{[4-(4-methyl-piperazin-1-yl)-phenylamino]-methylene}-2-oxo-2,3-dihydro-1H-indol-6-ylsulfanyl)-benzamide" |

These compounds may be prepared as follows:

Scheme I:

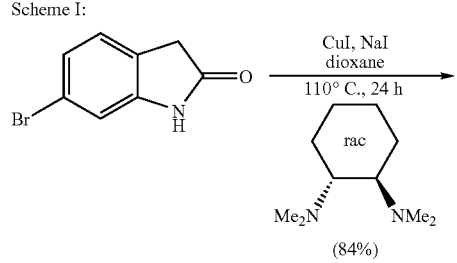

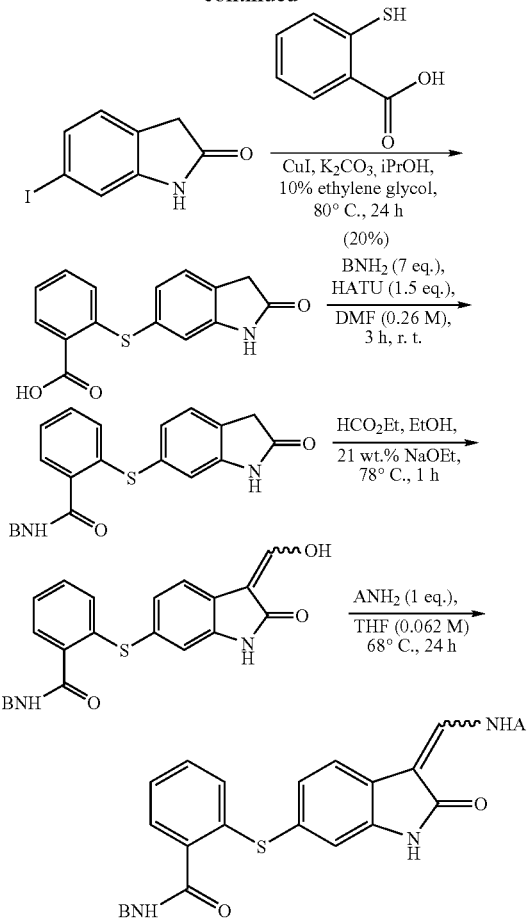

EXPERIMENTAL PROCEDURES

Preparation 1: 6-Iodooxindole

A schlenk tube and stir bar were dried in an oven overnight and then were evacuated, filled with $Ar_{(g)}$ and cooled. The schlenk tube was charged with CuI (45 mg, 0.236 mmol, 5 mol %), 6-bromoxindole (1.0 g, 4.72 mmol), and NaI (1.42 g, 9.44 mmol). The schlenk tube was evacuated and backfilled with $Ar_{(g)}$ (3 times). Racemic trans-N,N'-dimethyl-1,2-cyclohexanediamine (74 µL, 0.472 mmol, 10 mol %) and anhydrous dioxane (4.72 mL) were added via syringe under $Ar_{(g)}$. The schlenk tube was sealed with a teflon valve and the suspension was stirred at 110° C. for 24 h. The reaction was then cooled to room temperature and 15% $NH_4OH_{(aq)}$ (~50 mL) was added to the reaction mixture while stirring. The suspension was allowed to stir for about 30 min after which the tan solid was vacuum filtered and dried affording 6-Iodooxindole in 84% yield (1.027 g, 3.96 mmol).

Preparation 2:
(2-Oxo-2,3-dihydro-1H-indol-6-ylsulfanyl)-benzoic acid

CuI (40 mg, 0.05 mmol), potassium carbonate (1.66 g, 12 mmol), 6-iodooxindole (as prepared in Preparation 1; 1.0 g, 4.0 mmol) and 2-mercapto-benzoic acid (0.62 g, 4.0 mmol) were added to a dry schlenk tube. The tube was evacuated and refilled with Ar$_{(g)}$ (3 times). 2-Propanol (5.0 mL) and ethylene glycol (0.5 mL, 8.0 mmol) were injected into the schlenk tube. The schlenk tube was sealed with a teflon valve and was heated to 80° C. and stirred for over 24 hours. Subsequently the reaction mixture was allowed to reach room temperature then diluted with EtOAc (10 mL) and water (10 mL). The mixture was acidified of to a pH=3-4 with the addition of 1 M HCl$_{(aq)}$ and the organics were separated and set aside. The aqueous phase was washed with additional EtOAc (10 mL). The combined organic layers were dried over Na$_2$SO$_4$, filtered and concentrated in vacuo affording a yellow solid. The solid was then purified via flash silica gel chromatography (gradient eluant starting with 5% MeOH in CHCl$_3$ increasing to 10% MeOH in CHCl$_3$) affording the title compound as a pale yellow solid (0.228 g, 0.77 mmol, 20% yield).

Example 1

N-Methyl-3-(3-{[4-(4-methyl-piperazin-1-yl)-phenylamino]-methylene}-2-oxo-2,3-dihydro-1H-indol-6-ylsulfanyl)-benzamide A small screw cap test tube was charged with 3-(3-hydroxymethylene-2-oxo-2,3-dihydro-1H-indol-6-ylsulfanyl)-N-methyl-benzamide (as prepared below; 20 mg, 0.062 mmol) and THF (1 mL). To the resulting solution was added 4-(4-methyl-piperazin-1-yl)-phenylamine (12 mg, 0.062 mmol), and the mixture was stirred for 24 h at 68° C. Subsequently, the reaction mixture was cooled to room temperature and then concentrated in vacuo. Purification of the crude residue via flash silica gel chromatography (10% MeOH in CHCl$_3$) afforded the title compound in 39% yield (12 mg, 0.024 mmol).

3-(3-Hydroxymethylene-2-oxo-2,3-dihydro-1H-indol-6-ylsulfanyl)-N-methyl-benzamide was prepared from (2-Oxo-2,3-dihydro-1H-indol-6-ylsulfanyl)-benzoic acid 6-bromo-oxindole via the following multi-step procedure:

Step 1: Methyl-3-(2-oxo-2,3-dihydro-1H-indol-6-ylsulfanyl)-benzamide (2-Oxo-2,3-dihydro-1H-indol-6-ylsulfanyl)-benzoic acid (as prepared in Preparation 2; 0.228 g, 0.77 mmol) was dissolved in DMF (3 mL). The resulting solution was treated with HATU (0.434 g, 1.16 mmol) and 2M MeNH$_2$ in THF (2.68 mL, 5.36 mmol) then allowed to stir for 3 hours at room temperature. The reaction mixture was then concentrated in vacuo and the crude was re-dissolved in EtOAc (15 mL) and washed with brine (3×15 mL). The combined organics were then dried over Na$_2$SO$_4$, filtered and concentrated in vacuo. The crude mixture was then purified via flash silica gel chromatography (5% MeOH in CHCl$_3$) affording the title compound as a white solid in 31% yield (71 mg, 0.239 mmol).

Step 2: 3-(3-Hydroxymethylene-2-oxo-2,3-dihydro-1H-indol-6-ylsulfanyl)-N-methyl-benzamide Methyl-3-(2-oxo-2,3-dihydro-1H-indol-6-ylsulfanyl)-benzamide (as prepared in step 1 above; 0.71 g, 0.239 mmol) and ethyl formate (0.058 mL, 0.717 mmol) were dissolved in anhydrous ethanol (0.5 mL). The resulting solution was treated in dropwise fashion with a 21 wt % solution of sodium ethoxide in ethanol (0.446 mL, 1.20 mmol). This reaction mixture was heated at 78° C. for 1 h, producing a black oil. Subsequently, the reaction mixture was cooled to room temperature, and then the reaction pH was adjusted to pH=1 with dropwise addition of 1M HCl$_{(aq)}$. The reaction mixture was diluted with EtOAc (15 mL) and washed with brine (3×15 mL). The combined organics were then dried over Na$_2$SO$_4$, filtered and concentrated in vacuo. The crude residue was purified via flash silica gel chromatography (10% MeOH in CHCl$_3$) affording the title compound in 26% yield (0.020 g, 0.0621 mmol).

Example 2

N-Methyl-3-(3-{[4-(4-methyl-piperazin-1-yl)-phenylamino]-methylene}-2-oxo-2,3-dihydro-1H-indol-6-ylsulfanyl)-benzamide A 1 mL vial was charged with N-(2,5-Dimethyl-2H-pyrazol-3-yl)-2-{3-[1-hydroxy-meth-(Z)-ylidene]-2-oxo-2,3-dihydro-1H-indol-6-ylsulfanyl}-benzamide (as prepared below; 55 mg, 0.135 mmol), 4-(4-methyl-piperazin-1-yl)-phenylamine (25.8 mg, 0.138 mmol), and THF (1 mL). This reaction mixture was stirred for 24 h at 68° C. Subsequently, the reaction mixture was cooled to room temperature and concentrated in vacuo. The crude residue was re-suspended in EtOAc (5 mL) and extracted with H$_2$O (~5 mL). The organic layer was concentrated in vacuo and the residue was chromatographed via flash silica gel chromatography (gradient of 1-10% MeOH in CHCl$_3$) afforded the title compound in 35% yield (27 mg, 0.047 mmol).

N-(2,5-Dimethyl-2H-pyrazol-3-yl)-2-{3-[1-hydroxy-meth-(Z)-ylidene]-2-oxo-2,3-dihydro-1H-indol-6-ylsulfanyl}-benzamide was prepared from 6-iodo-oxindole via the following multi-step procedure:

Step 1: 2-Benzoylsulfanyl-benzoic acid

2-Mercapto-benzoic acid (1.5 g, 9.73 mmol) was dissolved in a solution of NaHCO$_3$ (2.6 g, 0.031 mol) in H$_2$O (25 mL). The 2-mercapto-benzoic acid solution was cooled to 0° C. Benzoyl chloride (1.36 g, 9.73 mmol) was then added followed by additional Na$_2$CO$_3$ (2.01 g, 14.60 mmol). The reaction mixture was stirred for 30 min at 0° C. and then, after allowing it to warm to room temperature, the reaction mixture was allowed to stir for an additional 45 minutes. Subsequently the reaction mixture was acidified with concentrated HCl forming a white precipitate. The precipitate was collected washed with cold water and dried in a vacuum dessicator overnight to yield the title compound in 83% yield (2.08 g, 8.08 mmol).

Step 2: Thiobenzoic acid S-[2-(2,5-dimethyl-2H-pyrazol-3-ylcarbamoyl)-phenyl]ester To a solution of 2-Benzoylsulfanyl-benzoic acid (as prepared in step 1 above; 1 g, 3.88 mmol) in anhydrous CH$_2$Cl$_2$ (40 mL), was added oxalyl chloride (2 mL, 22.5 mmol) followed by 2 drops of DMF. The suspension was stirred at room temperature until a clear solution was obtained. The solvent was evaporated under reduced pressure and the remaining crude solid was dissolved in anhydrous THF (40 mL). NEt$_3$ (0.29 g, 2.5 mmol) and 2,5-Dimethyl-2H-pyrazol-3-ylamine (0.432 g, 3.88 mmol) were then added and the solution was allowed to stir at 50° C. overnight. The reaction mixture was diluted with EtOAc (60 mL) and extracted with H$_2$O (3×50 mL) and saturated NaHCO$_{3(aq)}$. The organics were then dried over Na$_2$SO$_4$, filtered, concentrated in vacuo. The crude residue was purified via column chromatography (30% EtOAc/

Hexanes) to give pure thiobenzoic acid S-[2-(2,5-dimethyl-2H-pyrazol-3-ylcarbamoyl)-phenyl]ester in 71% yield (0.966 g, 2.75 mmol).

Step 3: N-(2,5-Dimethyl-2H-pyrazol-3-yl)-2-mercapto-benzamide

The thiobenzoic acid S-[2-(2,5-dimethyl-2H-pyrazol-3-ylcarbamoyl)-phenyl]ester (as prepared in step 2 above; 0.966 g, 2.75 mmol) was dissolved in THF (50 mL) and MeOH (100 mL). Under $N_{2(g)}$, a 0.2M solution of NaOH (80 mL) was added and the mixture was stirred for 1.5 h at rt. A saturated solution of $NaHCO_{3(aq)}$ (100 mL) was added and the aqueous layer was extracted with $CHCl_3$ (3×100 mL). The combined organic layers were dried over $Na_2SO_4$, filtered and evaporated in vacuo. The crude mixture was then purified over silica (5% MeOH/$CHCl_3$) to give the title compound in 67% yield (0.455 g, 1.84 mmol).

Step 4: N-(2,5-Dimethyl-2H-pyrazol-3-yl)-2-(2-oxo-2,3-dihydro-1H-indol-6-ylsulfanyl)-benzamide CuI (40 mg, 0.05 mmol), potassium carbonate (1.66 g, 12 mmol), 6-iodooxindole (as prepared in Preparation 1; 0.5 g, 1.93 mmol) and N-(2,5-Dimethyl-2H-pyrazol-3-yl)-2-mercapto-benzamide (as prepared in step 3 above; 0.477 g, 1.93 mmol) were added to a dry schlenk tube. The tube was evacuated and refilled with $Ar_{(g)}$ (3 times). Isopropanol (3.0 mL) and ethylene glycol (0.250 mL) were injected into the schlenk tube. The schlenk tube was sealed with a teflon valve and was heated to 80° C. and stirred for over 24 hours. Subsequently the reaction mixture was allowed to reach room temperature then diluted with EtOAc (~20 mL) and water (~10 mL). The mixture was acidified with 1 M $HCl_{(aq)}$ and the organics were separated and set aside. The aqueous phase was washed with EtOAc (2×20 mL). The organic layers were combined, dried over silica gel, filtered and concentrated in vacuo affording a yellow solid. The solid was then purified via flash silica gel chromatography (gradient eluant 10 to 40% EtOAc in Hexanes) affording the title compound as a pale yellow solid (0.379 g, 1.01 mmol, 52% yield).

Step 5: N-(2,5-Dimethyl-2H-pyrazol-3-yl)-2-{3-[1-hydroxy-meth-(Z)-ylidene]-2-oxo-2,3-dihydro-1H-indol-6-ylsulfanyl}-benzamide N-(2,5-Dimethyl-2H-pyrazol-3-yl)-2-(2-oxo-2,3-dihydro-1H-indol-6-ylsulfanyl)-benzamide (as prepared above in Step 4; 0.300 g, 0.793 mmol) was dissolved in anhydrous ethanol (8 mL) and the resulting solution was treated with ethyl formate (0.058 mL, 0.717 mmol) The resulting solution was treated in dropwise fashion with a 21 wt % solution of sodium ethoxide in ethanol (1.48 mL, 3.97 mmol). This reaction mixture was heated at 78° C. for 0.5 h, which caused the reaction mixture to turn black in color. Subsequently, the reaction mixture was cooled to room temperature, and then the reaction pH was adjusted to pH=1 with dropwise addition of 1M $HCl_{(aq)}$. The reaction mixture was diluted with EtOAc (25 mL) and extracted with brine (2×25 mL). The organic layer was dried over sodium sulfate, filtered and concentrated in vacuo. The crude product was purified via flash silica gel chromatography (5% MeOH in $CHCl_3$) affording the title compound in 19% yield (0.061 g, 0.150 mmol).

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of Catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

All references cited herein are hereby incorporated by reference in their entirety.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof.

What is claimed is:

1. A compound represented by the following general formulas:

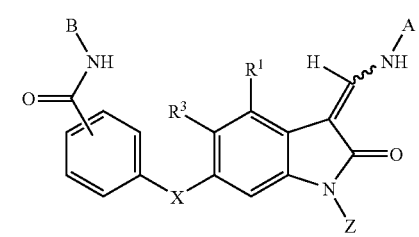

I

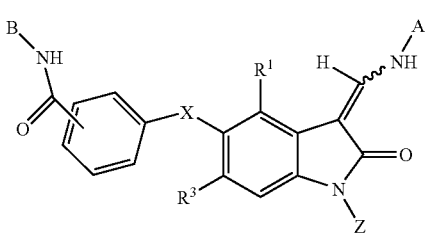

II wherein X is selected from the group consisting of C=O, C=S, $CR^4R^5$, O, S, NH, and $NR^4$;

Z is selected from the group consisting of hydrogen, $C_1$ to $C_8$ alkyl, phenyl, hydroxymethyl, —$CH_2$—N(—$CH_2CH_2W$ $CH_2CH_2$—), $COCH_3$, $CH_2CH_2OH$, and $CH_2CH_2CH_2OH$;

W is selected from the group consisting of O, S, $CH_2$ and $NCH_3$;

$R^1$ is selected from the group consisting of hydrogen and $CH_3$;

$R^3$ is selected from the group consisting of hydrogen, $C_1$ to $C_8$ alkyl, phenyl, hydroxymethyl, $COCH_3$, $CH_2CH_2OH$, $CH_2CH_2CH_2OH$, and $[C(R^2)_2]_cN(R^2)_2$, wherein $R^2$ is selected from the group consisting of hydrogen, halogen, $NO_2$, CN, $C_1$ to $C_4$ alkyl, aryl, or $N(R^2)_2$ may form a 3 to 7 membered heterocyclic ring, and said heterocyclic ring may be substituted with one or more of $R^2$, or $[C(R^2)_2]_c$ may form a 3 to 7 membered carbocyclic or heterocyclic ring;

$R^4$ and $R^5$ are selected from the group consisting of hydrogen, halogen, $NO_2$, CN, $C_1$ to $C_8$ alkyl and aryl; or $CR^4R^5$ may form a 3 to 7 membered carbocyclic or heterocyclic ring;

A is

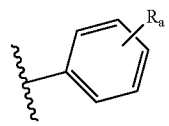

wherein,

R is selected from the group consisting of hydrogen, halogen, $C_1$ to $C_8$ alkyl, $CF_3$, $OCF_3$, $OCF_2H$, $CH_2CN$, CN, $SR^2$, $(CR^7R^8)_cC(O)OR^2$, $C(O)N(R^2)_2$, $(CR^7R^8)_cOR^2$, $HNC(O)R^2$, HN —$C(O)OR^2$, $(CR^7R^8)_cOC(O)$ $(CR^7R^8)_c$ $N(R^2)_2$, $(CR^7R^8)_cN(R^2)_2$, $SO_2$ $(CR^7R^8)_cN$ $(R^2)_2$, $OP(O)(OR^2)_2$, $OC(O)OR^2$, $OCH_2O$, HN—CH=CH, —$N(COR^2)CH_2CH_2$, HC=N—NH, N=CH—S, $O(CR^7R^8)_d$—$R^6$, $(CR^7R^8)_c$—$R^6$ and $(CR^7R^8)_cNR_2(CR^7R^8)_dR^6$ wherein $R^6$ is selected from the group consisting of halogen, 3-fluoropyrrolidinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5(4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino) pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N-BOC-pyrrolidinyl, 4-amino-1,2,2,6,6-pentamethylpiperidinyl, 4-aminomethyltetrahydropyran, ethanolamine and alkyl-substituted derivatives thereof; provided said alkyl or phenyl radicals may be substituted with one or two halo, hydroxy or lower alkyl amino radicals or said alkyl radicals may include enchained nitrogen or oxygen atoms, i.e. oxa or imino radicals, as, and wherein $R^7$ and $R^8$ are selected from the group consisting of H, hydroxyl, halogen and $C_1$ to $C_4$ alkyl or $CR^7R^8$ may represent a carbocyclic ring of from 3 to 6 carbons;

B is selected from the group consisting of hydrogen, hydroxy, $C_1$ to $C_8$ alkyl, aryl and $CR^4R^5$ wherein $CR^4R^5$ forms a 3 to 7 membered carbocyclic or heterocyclic ring, a is 0 or an integer of from 1 to 5, preferably 1 to 3;

c is 0 or an integer of from 1 to 4, d is an integer of from 2 to 5;

the wavy line represents a E or Z bond and pharmaceutically acceptable salts thereof.

2. The compound of claim 1 wherein X is S.

3. The compound of claim 2 wherein R is piperazinyl.

4. The compound of claim 3 wherein B is methyl or 2,5-dimethyl-2H-pyrazol-3-yl.

5. The compound of claim 4 wherein the compound is N-methyl-2-(3-{[4-(4-methyl-piperazin-1-yl)-phenylamino]-methylene}-2-oxo-2,3-dihydro-1H-indol-6-ylsulfanyl)-benzamide.

6. The compound of claim 4 wherein the compound is N-(2,5-dimethyl-2H-pyrazol-3-yl)-2-(3-{[4-(4-methyl-piperazin-1-yl)-phenylamino]-methylene}-2-oxo-2,3-dihydro-1H-indol-6-ylsulfanyl)-benzamide.

7. The compound of claim 1 wherein B is selected from the group consisting of 5 or 6 membered aryl rings represented by formula III below

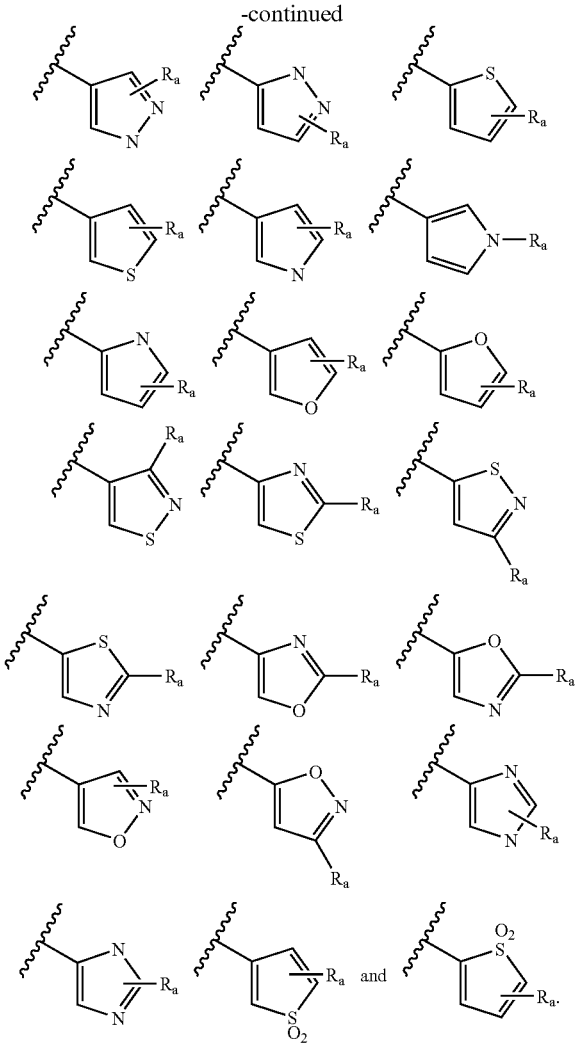

* * * * *

UNITED STATES PATENT AND TRADEMARK OFFICE
CERTIFICATE OF CORRECTION

PATENT NO. : 7,439,371 B2  
APPLICATION NO. : 11/456630  
DATED : October 21, 2008  
INVENTOR(S) : Wurster et al.

Page 1 of 1

It is certified that error appears in the above-identified patent and that said Letters Patent is hereby corrected as shown below:

Title page, number (54) and col. 1; Delete "INDOL".

In column 2, line 9, delete "phophorylation" and insert -- phosphorylation --, therefor.

In column 10, line 47-48, delete "dessicator" and insert -- desiccator --, therefor.

Signed and Sealed this

Third Day of February, 2009

JOHN DOLL  
*Acting Director of the United States Patent and Trademark Office*